US007754852B2

(12) United States Patent
Burnett, Jr. et al.

(10) Patent No.: US 7,754,852 B2
(45) Date of Patent: Jul. 13, 2010

(54) NATRIURETIC POLYPEPTIDES

(75) Inventors: John C. Burnett, Jr., Rochester, MN (US); Candace Y. W. Lee, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 0 days.

(21) Appl. No.: 12/175,779

(22) Filed: Jul. 18, 2008

(65) Prior Publication Data

US 2009/0054337 A1 Feb. 26, 2009

Related U.S. Application Data

(60) Provisional application No. 60/951,117, filed on Jul. 20, 2007.

(51) Int. Cl.
*A61K 38/00* (2006.01)
(52) U.S. Cl. .......................................... 530/324; 514/12
(58) Field of Classification Search ........................ None
See application file for complete search history.

(56) References Cited

U.S. PATENT DOCUMENTS

| 4,034,074 | A | 7/1977 | Miles |
| 4,098,876 | A | 7/1978 | Piasio et al. |
| 4,233,402 | A | 11/1980 | Maggio et al. |
| 5,296,347 | A | 3/1994 | LaMotte, III |
| 5,449,751 | A * | 9/1995 | Forssmann et al. .......... 530/324 |
| 5,580,859 | A | 12/1996 | Felgner et al. |
| 5,589,466 | A | 12/1996 | Felgner et al. |
| 2006/0172933 | A1 | 8/2006 | James et al. |
| 2006/0293232 | A1 | 12/2006 | Levy et al. |

FOREIGN PATENT DOCUMENTS

| WO | WO 98/45329 | * 10/1998 |
| WO | WO 01/44284 | 6/2001 |
| WO | WO 2006/110743 | 10/2006 |

OTHER PUBLICATIONS

Agulló et al., "Effect of ischemia on soluble and particulate guanylyl cyclase-mediated cGMP synthesis in cardiomyocytes," *Am. J. Physiol. Heart Circ. Physiol.*, 2003, 284:H2170-H2176.
Ahluwalia et al., "Vascular actions of natriuretic peptides. Cyclic GMP-dependent and -independent mechanisms," *Basic Res. Cardiol.*, 2004, 99:83-89.
Bryan et al., "Renal hyporesponsiveness to atrial natriuretic peptide in congestive heart failure results from reduced atrial natriuretic peptide receptor concentrations," *Am. J. Physiol. Renal Physiol.*, 2007, 292:F1636-F1644.
Carstens et al., "Metabolism and action of urodilatin infusion in healthy volunteers," *Clin. Pharmacol. Ther.*, 1998, 64:73-86.
Chauhan et al., "Release of C-type natriuretic peptide accounts for the biological activity of endothelium-derived hyperpolarizing factor," *Proc. Natl. Acad. Sci. USA*, 2003, 100(3):1426-1431.

Chaurand et al., "Peptide and Protein Identification by Matrix-Assisted Laser Desorption Ionization (MALDI) and MALDI-Post-Source Decay Time-of-Flight Mass Spectrometry," *J. Am. Soc. Mass Spectrom.*, 1999, 10:91-103.
Chen and Burnett, Jr., "Clinical application of the natriuretic peptides in heart failure," *Eur. Heart J. Suppl.*, 2006, 8(Suppl E):E18-E25.
Cole et al., "The EBV-Hybridoma Technique and its Application to Human Lung Cancer," *Monoclonal Antibodies and Cancer Therapy*, 1983, Alan R. Liss, Inc., pp. 77-96.
Cote et al., "Generation of human monoclonal antibodies reactive with cellular antigens," *Proc. Natl. Acad. Sci. USA*, 1983, 80:2026-2030.
Del Ry et al., "C-type natriuretic peptide and heart failure," *Pharmacol. Res.*, 2006, 54:326-333.
Dickey et al., "Novel bifunctional natriuretic peptides as potential therapeutics," *J. Biol. Chem.*, 2008, 283(50):35003-35009.
Dorner et al., "Hemodynamic effects of continuous urodilatin infusion: A dose finding study," *Clin. Pharmacol. Ther.*, 1998, 64:322-330.
Forssmann et al., "The renal urodilatin system: clinical implications," *Cardiovasc. Res.*, 2001, 51:450-462.
Furuya et al., "C-type natriuretic peptide is a growth inhibitor of rat vascular smooth muscle cells," *Biochem. Biophys. Res. Commun.*, 1991, 177(3):927-931.
Furuya et al., "Structural requirements of C-type natriuretic peptide for elevation of cyclic GMP in cultured vascular smooth muscle cells," *Biochem. Biophys. Res. Commun.*, 1992,183(3):964-969.
Gagelmann et al., "Urodilatin (CDD/ANP-95-126) is not biologically inactivated by a peptidase from dog kidney cortex membranes in contrast to atrial natriuretic peptide/cardiodilatin (α-hANP/CDD-99-126)," *FEBS Lett.*, 1988, 233(2):249-254.
Gevaert et al., "Protein identification based on matrix assisted laser desorption/ionization-post source decay-mass spectrometry," *Electrophoresis*, 2001, 22(9):1645-1651.
Gheorghiade et al., "Navigating the Crossroads of Coronary Artery Disease and Heart Failure," *Circulation*, 2006,114:1202-1213.
Goetz et al., "Evidence that Urodilatin, Rather Than ANP, Regulates Renal Sodium Excretion," *J. Am. Soc. Nephrol.*,1990, 1:867-874.
Guatelli et al., "Isothermal, in vitro amplification of nucleic acids by a multienzyme reaction modeled after retroviral replication," *Proc. Natl. Acad. Sci. USA*, 1990, 87:1874-1878.
Hirsch et al., "ANP and Urodilatin: Who Is Who in the Kidney," *Eur. J. Med. Res.*, 2006, 11:447-454.
Hobbs et al., "Natriuretic Peptide Receptor-C Regulates Coronary Blood Flow and Prevents Myocardial Ischemia/Reperfusion Injury. Novel Cardioprotective Role for Endothelium-Derived C-Type Natriuretic Peptide," *Circulation*, 2004, 110:1231-1235.

(Continued)

*Primary Examiner*—Suzanne M. Noakes
(74) *Attorney, Agent, or Firm*—Fish & Richardson P.C.

(57) ABSTRACT

This document provides natriuretic polypeptides. For example, this document provides polypeptides having a natriuretic activity. In some cases, a polypeptide provided herein can have natriuretic activities, while lacking the ability to lower blood pressure. This document also provides methods and materials for inducing natriuretic activities within a mammal.

19 Claims, 5 Drawing Sheets

OTHER PUBLICATIONS

Hunt et al., "Bioactivity and Metabolism of C-Type Natriuretic Peptide in Normal Man," *J. Clin. Endocrinol. Metab.*, 1994, 78:1428-1435.

Huse et al., "Generation of a large combinatorial library of the immunoglobulin repertoire in phage lambda," *Science*, 1989, 246:1275-1281.

Hyrup et al.; "Peptide nucleic acids (PNA): synthesis, properties and potential applications," *Bioorgan. Med. Chem.*, 1996, 4:5-23.

Inserte et al., "Urodilatin limits acute reperfusion injury in the isolated rat heart," *Cardiovasc. Res.*, 2000, 45:351-359.

Kitakaze et al., "Large-Scale Trial Using Atrial Natriuretic Peptide or Nicorandil as an Adjunct to Percutaneous Coronary Intervention for ST-Segment Elevation Acute Myocardial Infarction," *Circulation*, 2006, 114(22):2425-2426.

Köhler and Milstein, "Continuous cultures of fused cells secreting antibody of predefined specificity," *Nature*, 1975, 256:495-497.

Kozbor et al., "The Production of Monoclonal Antibodies from Human Lymphocytes," *Immunology Today*, 1983, 4:72-79.

Lee and Burnett, Jr., "Natriuretic.peptides and therapeutic application," *Heart Failure Rev.*, 2007, 12(2):131-142.

Lewis, "Oncogenes Can Work Together to Increase Pathogenic Effects," *Genetic Engineering News*, 1992, 12(9):1.

Lee et al., "Renal and Neurohumoral Actions of a Novel Chimeric Natriuretic Peptide, CD-NP," 2007, Late-breaking abstract accepted for the Annual Meeting of the American Society for Clinical Pharmacology and Therapeutics Meeting, Mar. 21-24, 2007.

Lisy and Burnett, Jr., "The Design, Synthesis and Cardiorenal Actions of a New Chimeric Natriuretic Peptide CD-NP," [abst], *J. Am. Coll. Cardiol.*, 2003, 41(6 Suppl 1):312A.

Mentzer et al., "Effects of perioperative nesiritide in patients with left ventricular dysfunction undergoing cardiac surgery: The NAPA Trial," *J. Am. Coll. Cardiol.*, 2007, 49(6):716-726.

Mitrovic et al., "Effects of the renal natriuretic peptide urodilatin (ularitide) in patients with decompensated chronic heart failure: A double-blind, placebo-controlled, ascending-dose trial," *Am. Heart J.*, 2005, 150(6):1239.

Mitrovic et al., "Haemodynamic and clinical effects of ularitide in decompensated heart failure," *Eur. Heart J.*, 2006, 27:2823-2832.

Nir et al., "CNP is present in canine renal tubular cells and secreted by cultured opossum kidney cells," *Am. J. Physiol.*, 1994, 267(6 Pt 2):R1653-R1657.

Padilla et al., "Intravenous administration of the natriuretic peptide urodilatin at low doses during coronary reperfusion limits infarct size in anesthetized pigs," *Cardiovasc. Res.*, 2001, 51(3):592-600.

Potter et al., "Natriuretic Peptides, Their Receptors, and Cyclic Guanosine Monophosphate-Dependent Signaling Functions," *Endocrine Rev.*, 2006, 27:47-72.

Publication Committee for the VMAC Investigators (Vasodilation in the Management of Acute CHF), "Intravenous Nesiritide vs Nitroglycerin for Treatment of Decompensated Congestive Heart Failure. A Randomized Controlled Trial," *JAMA*, 2002, 287(120:1531-1540 [Erratum, JAMA, 2002;1288:1577].

Sackner-Bernstein et al., "Risk of Worsening Renal Function With Nesiritide in Patients With Acutely Decompensated Heart Failure," *Circulation*, 2005, 111:1487-1491.

Schulz-Knappe et al., "Isolation and Structural Analysis of "Urodilatin", a New Peptide of the Cardiodilatin-(ANP)-Family, Extracted from Human Urine," *Klin Wochenschr.*, 1988, 66:752-759.

Schweitz et al., "A New Member of the Natriuretic Peptide Family Is Present in the Venom of the Green Mamba (*Dendroaspis angusticeps*)," *J. Biol. Chem.*, 1992, 267(20):13928-13932.

Scotland et al., "C-type natriuretic peptide inhibits leukocyte recruitment and platelet-leukocyte interactions via suppression of P-selectin expression," *Proc. Natl. Acad. Sci. USA*, 2005, 102(40):14452-14457.

Singh et al., "Novel Snake Venom Ligand Dendroaspis Natriuretic Peptide Is Selective for Natriuretic Peptide Receptor-A in Human Heart. Downregulation of Natriuretic Peptide Receptor-A in Heart Failure," *Circ. Res.*, 2006, 99(2):183-190.

Stingo et al., "Cardiovascular and renal actions of C-type natriuretic peptide," *Am. J. Physiol.*, 1992, 262(1 Pt 2):H308-H312.

Stingo et al., "Presence of C-type natriuretic peptide in cultured human endothelial cells and plasma," *Am. J. Physiol.*, 1992, 263(4 Pt 2):H1318-H1321.

Sudoh et al., "C-type natriuretic peptide (CNP): a new member of natriuretic peptide family identified in porcine brain," *Biochem. Biophys. Res. Commun.*, 1990, 168(2):863-870.

Summerton and Weller, "Morpholino antisense oligomers: design, preparation, and properties," *Antisense Nucleic Acid Drug Dev.*, 1997, 7:187-195.

Suwa et al., "Multicenter Prospective Investigation on Efficacy and Safety of Carperitide for Acute Heart Failure in the 'Real World' of Therapy," *Circ. J.*, 2005, 69(3):283-290.

Villar et al., "Definitive role for natriuretic peptide receptor-C in mediating the vasorelaxant activity of C-type natriuretic peptide and endothelium-derived hyperpolarising factor," *Cardiovasc. Res.*, 2007, 74:515-525.

Wei et al., "Action of C-type natriuretic peptide in isolated canine arteries and veins," *Am. J. Physiol.*, 1993, 264(1 Pt 2):H71-H73.

Wei et al., "Vasonatrin peptide: a unique synthetic natriuretic and vasorelaxing peptide," *J. Clin. Invest.*, 1993, 92(4):2048-2052.

Weiss, "Hot prospect for new gene amplifier," *Science*, 1991, 254(5036):1292-1293.

\* cited by examiner

SEQUENCE LISTING

```
<160> NUMBER OF SEQ ID NOS: 4

<210> SEQ ID NO 1
<211> LENGTH: 10
<212> TYPE: PRT
<213> ORGANISM: Homo sapiens

<400> SEQUENCE: 1

Thr Ala Pro Arg Ser Leu Arg Arg Ser Ser
1               5                   10

<210> SEQ ID NO 2
<211> LENGTH: 17
<212> TYPE: PRT
<213> ORGANISM: Homo sapiens

<400> SEQUENCE: 2

Cys Phe Gly Leu Lys Leu Asp Arg Ile Gly Ser Met Ser Gly Leu Gly
1               5                   10                  15

Cys

<210> SEQ ID NO 3
<211> LENGTH: 5
<212> TYPE: PRT
<213> ORGANISM: Homo sapiens

<400> SEQUENCE: 3

Asn Ser Phe Arg Tyr
1               5

<210> SEQ ID NO 4
<211> LENGTH: 32
<212> TYPE: PRT
<213> ORGANISM: Artificial Sequence
<220> FEATURE:
<223> OTHER INFORMATION: synthetic peptide

<400> SEQUENCE: 4

Thr Ala Pro Arg Ser Leu Arg Arg Ser Ser Cys Phe Gly Leu Lys Leu
1               5                   10                  15

Asp Arg Ile Gly Ser Met Ser Gly Leu Gly Cys Asn Ser Phe Arg Tyr
            20                  25                  30
```

NATRIURETIC POLYPEPTIDES

CROSS-REFERENCE TO RELATED APPLICATIONS

This application claims benefit of priority from U.S. Provisional Application Ser. No. 60/951,117, filed on Jul. 20, 2007.

STATEMENT AS TO FEDERALLY SPONSORED RESEARCH

This invention was made with government support under grant HL036634 awarded by the National Institutes of Heart, Lung, and Blood Institute. The government has certain rights in the invention.

BACKGROUND

1. Technical Field

This document relates to natriuretic polypeptides. For example, this document provides methods and materials related to natriuretic polypeptides and the use of natriuretic polypeptides to treat cardiovascular and renal conditions.

2. Background Information

Natriuretic polypeptides are polypeptides that can cause natriuresis (increased sodium excretion in the urine). Such polypeptides can be produced by brain, heart, kidney, and/or vasculature tissue.

SUMMARY

This document relates to natriuretic polypeptides. For example, this document provides methods and materials related to natriuretic polypeptides and the use of natriuretic polypeptides to treat cardiovascular conditions, renal conditions, or both cardiovascular conditions and renal conditions. In some cases, a polypeptide provided herein can have diuretic activity, natriuretic activity, the ability to activate cGMP, the ability to increase glomerular filtration rate, the ability to reduce renin production, the ability to reduce angiotensin production, the ability to reduce aldosterone production, the ability to reduce abnormally elevated cardiac filling pressures, the ability to optimize renal blood flow, or a combination thereof. In some cases, a polypeptide provided herein can increase endogenous ANP, BNP, and CNP levels. In some cases, a polypeptide provided herein can lack the ability to lower blood pressure and can lack the ability to cause systemic hypotension. In some cases, a polypeptide provided herein can be an agonist for natriuretic peptide receptor-A, natriuretic peptide receptor-B, or both natriuretic peptide receptor-A and natriuretic peptide receptor-B.

In general, one aspect of this document features a polypeptide less than 44 amino acid residues in length, wherein the polypeptide comprises, in an order from amino terminus to carboxy terminus: (a) the sequence set forth in SEQ ID NO:1 or the sequence set forth in SEQ ID NO:1 with no more than three additions, subtractions, or substitutions, (b) the sequence set forth in SEQ ID NO:2 or the sequence set forth in SEQ ID NO:2 with no more than five additions, subtractions, or substitutions, and (c) the sequence set forth in SEQ ID NO:3 or the sequence set forth in SEQ ID NO:3 with no more than three additions, subtractions, or substitutions. The polypeptide can comprise natriuretic activity. The polypeptide can lack the ability to induce systemic hypotension. The polypeptide can comprise the sequence set forth in SEQ ID NO:1. The polypeptide can comprise the sequence set forth in SEQ ID NO:2. The polypeptide can comprise the sequence set forth in SEQ ID NO:3. The polypeptide can comprise the sequence set forth in SEQ ID NO:1, the sequence set forth in SEQ ID NO:2, and the sequence set forth in SEQ ID NO:3. The polypeptide can comprise the sequence set forth in SEQ ID NO:1 with no more than three conservative amino acid substitutions. The polypeptide can comprise the sequence set forth in SEQ ID NO:2 with no more than five conservative amino acid substitutions. The polypeptide can comprise the sequence set forth in SEQ ID NO:3 with no more than three conservative amino acid substitutions. The polypeptide can be a substantially pure polypeptide.

In another aspect, this document features an isolated nucleic acid encoding a polypeptide less than 44 amino acid residues in length, wherein the polypeptide comprises, in an order from amino terminus to carboxy terminus: (a) the sequence set forth in SEQ ID NO:1 or the sequence set forth in SEQ ID NO:1 with no more than three additions, subtractions, or substitutions, (b) the sequence set forth in SEQ ID NO:2 or the sequence set forth in SEQ ID NO:2 with no more than five additions, subtractions, or substitutions, and (c) the sequence set forth in SEQ ID NO:3 or the sequence set forth in SEQ ID NO:3 with no more than three additions, subtractions, or substitutions. The polypeptide can comprise natriuretic activity. The polypeptide can lack the ability to induce systemic hypotension. The polypeptide can comprise the sequence set forth in SEQ ID NO:1. The polypeptide can comprise the sequence set forth in SEQ ID NO:2. The polypeptide can comprise the sequence set forth in SEQ ID NO:3. The polypeptide can comprise the sequence set forth in SEQ ID NO:1, the sequence set forth in SEQ ID NO:2, and the sequence set forth in SEQ ID NO:3. The polypeptide can comprise the sequence set forth in SEQ ID NO:1 with no more than three conservative amino acid substitutions. The polypeptide can comprise the sequence set forth in SEQ ID NO:2 with no more than five conservative amino acid substitutions. The polypeptide can comprise the sequence set forth in SEQ ID NO:3 with no more than three conservative amino acid substitutions. The polypeptide can be a substantially pure polypeptide.

In another aspect, this document features a vector comprising a nucleic acid encoding a polypeptide less than 44 amino acid residues in length, wherein the polypeptide comprises, in an order from amino terminus to carboxy terminus: (a) the sequence set forth in SEQ ID NO:1 or the sequence set forth in SEQ ID NO:1 with no more than three additions, subtractions, or substitutions, (b) the sequence set forth in SEQ ID NO:2 or the sequence set forth in SEQ ID NO:2 with no more than five additions, subtractions, or substitutions, and (c) the sequence set forth in SEQ ID NO:3 or the sequence set forth in SEQ ID NO:3 with no more than three additions, subtractions, or substitutions. The polypeptide can comprise natriuretic activity. The polypeptide can lack the ability to induce systemic hypotension. The polypeptide can comprise the sequence set forth in SEQ ID NO:1. The polypeptide can comprise the sequence set forth in SEQ ID NO:2. The polypeptide can comprise the sequence set forth in SEQ ID NO:3. The polypeptide can comprise the sequence set forth in SEQ ID NO:1, the sequence set forth in SEQ ID NO:2, and the sequence set forth in SEQ ID NO:3. The polypeptide can comprise the sequence set forth in SEQ ID NO:1 with no more than three conservative amino acid substitutions. The polypeptide can comprise the sequence set forth in SEQ ID NO:2 with no more than five conservative amino acid substitutions. The polypeptide can comprise the sequence set forth in SEQ ID NO:3 with no more than three conservative amino acid substitutions. The polypeptide can be a substantially pure polypeptide.

In another aspect, this document features a host cell comprising a nucleic acid encoding a polypeptide less than 44 amino acid residues in length, wherein the polypeptide comprises, in an order from amino terminus to carboxy terminus: (a) the sequence set forth in SEQ ID NO:1 or the sequence set forth in SEQ ID NO:1 with no more than three additions, subtractions, or substitutions, (b) the sequence set forth in SEQ ID NO:2 or the sequence set forth in SEQ ID NO:2 with no more than five additions, subtractions, or substitutions, and (c) the sequence set forth in SEQ ID NO:3 or the sequence set forth in SEQ ID NO:3 with no more than three additions, subtractions, or substitutions. The polypeptide can comprise natriuretic activity. The polypeptide can lack the ability to induce systemic hypotension. The polypeptide can comprise the sequence set forth in SEQ ID NO:1. The polypeptide can comprise the sequence set forth in SEQ ID NO:2. The polypeptide can comprise the sequence set forth in SEQ ID NO:3. The polypeptide can comprise the sequence set forth in SEQ ID NO:1, the sequence set forth in SEQ ID NO:2, and the sequence set forth in SEQ ID NO:3. The polypeptide can comprise the sequence set forth in SEQ ID NO:1 with no more than three conservative amino acid substitutions. The polypeptide can comprise the sequence set forth in SEQ ID NO:2 with no more than five conservative amino acid substitutions. The polypeptide can comprise the sequence set forth in SEQ ID NO:3 with no more than three conservative amino acid substitutions. The polypeptide can be a substantially pure polypeptide. The host cell can be a eukaryotic host cell.

In another aspect, this document features a pharmaceutical composition comprising a pharmaceutically acceptable carrier and a polypeptide less than 44 amino acid residues in length, wherein the polypeptide comprises, in an order from amino terminus to carboxy terminus: (a) the sequence set forth in SEQ ID NO:1 or the sequence set forth in SEQ ID NO:1 with no more than three additions, subtractions, or substitutions, (b) the sequence set forth in SEQ ID NO:2 or the sequence set forth in SEQ ID NO:2 with no more than five additions, subtractions, or substitutions, and (c) the sequence set forth in SEQ ID NO:3 or the sequence set forth in SEQ ID NO:3 with no more than three additions, subtractions, or substitutions. The polypeptide can comprise natriuretic activity. The polypeptide can lack the ability to induce systemic hypotension. The polypeptide can comprise the sequence set forth in SEQ ID NO:1. The polypeptide can comprise the sequence set forth in SEQ ID NO:2. The polypeptide can comprise the sequence set forth in SEQ ID NO:3. The polypeptide can comprise the sequence set forth in SEQ ID NO:1, the sequence set forth in SEQ ID NO:2, and the sequence set forth in SEQ ID NO:3. The polypeptide can comprise the sequence set forth in SEQ ID NO:1 with no more than three conservative amino acid substitutions. The polypeptide can comprise the sequence set forth in SEQ ID NO:2 with no more than five conservative amino acid substitutions. The polypeptide can comprise the sequence set forth in SEQ ID NO:3 with no more than three conservative amino acid substitutions. The polypeptide can be a substantially pure polypeptide.

In another aspect, this document features a method for increasing natriuretic activity within a mammal without lowering blood pressure. The method comprises administering to the mammal a polypeptide less than 44 amino acid residues in length, wherein the polypeptide comprises, in an order from amino terminus to carboxy terminus: (a) the sequence set forth in SEQ ID NO:1 or the sequence set forth in SEQ ID NO:1 with no more than three additions, subtractions, or substitutions, (b) the sequence set forth in SEQ ID NO:2 or the sequence set forth in SEQ ID NO:2 with no more than five additions, subtractions, or substitutions, and (c) the sequence set forth in SEQ ID NO:3 or the sequence set forth in SEQ ID NO:3 with no more than three additions, subtractions, or substitutions. The polypeptide can comprise natriuretic activity. The polypeptide can lack the ability to induce systemic hypotension. The polypeptide can comprise the sequence set forth in SEQ ID NO:1. The polypeptide can comprise the sequence set forth in SEQ ID NO:2. The polypeptide can comprise the sequence set forth in SEQ ID NO:3. The polypeptide can comprise the sequence set forth in SEQ ID NO:1, the sequence set forth in SEQ ID NO:2, and the sequence set forth in SEQ ID NO:3. The polypeptide can comprise the sequence set forth in SEQ ID NO:1 with no more than three conservative amino acid substitutions. The polypeptide can comprise the sequence set forth in SEQ ID NO:2 with no more than five conservative amino acid substitutions. The polypeptide can comprise the sequence set forth in SEQ ID NO:3 with no more than three conservative amino acid substitutions. The polypeptide can be a substantially pure polypeptide.

In another aspect, this document features a method for treating a mammal having a cardiovascular condition or renal condition. The method comprises administering to the mammal a polypeptide less than 44 amino acid residues in length under conditions wherein the severity of a manifestation of the cardiovascular condition or renal condition is reduced, wherein the polypeptide comprises, in an order from amino terminus to carboxy terminus: (a) the sequence set forth in SEQ ID NO:1 or the sequence set forth in SEQ ID NO:1 with no more than three additions, subtractions, or substitutions, (b) the sequence set forth in SEQ ID NO:2 or the sequence set forth in SEQ ID NO:2 with no more than five additions, subtractions, or substitutions, and (c) the sequence set forth in SEQ ID NO:3 or the sequence set forth in SEQ ID NO:3 with no more than three additions, subtractions, or substitutions. The polypeptide can comprise natriuretic activity. The polypeptide can lack the ability to induce systemic hypotension. The polypeptide can comprise the sequence set forth in SEQ ID NO:1. The polypeptide can comprise the sequence set forth in SEQ ID NO:2. The polypeptide can comprise the sequence set forth in SEQ ID NO:3. The polypeptide can comprise the sequence set forth in SEQ ID NO:1, the sequence set forth in SEQ ID NO:2, and the sequence set forth in SEQ ID NO:3. The polypeptide can comprise the sequence set forth in SEQ ID NO:1 with no more than three conservative amino acid substitutions. The polypeptide can comprise the sequence set forth in SEQ ID NO:2 with no more than five conservative amino acid substitutions. The polypeptide can comprise the sequence set forth in SEQ ID NO:3 with no more than three conservative amino acid substitutions. The polypeptide can be a substantially pure polypeptide. Administration of the polypeptide to the mammal can be such that it does not lower the blood pressure of the mammal.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DETAILED DESCRIPTION

This document relates to natriuretic polypeptides. For example, this document provides methods and materials related to natriuretic polypeptides and the use of natriuretic polypeptides to treat cardiovascular conditions (e.g., acute decompensated heart failure, acute coronary syndromes, and ventricular remodeling post-myocardial infarction) and renal conditions (e.g., perioperative renal dysfunction, renal dysfunction secondary to heart failure, and diabetic nephropathy).

In some cases, a polypeptide provided herein can have diuretic activity, natriuretic activity, the ability to activate cGMP, the ability to increase glomerular filtration rate, the ability to reduce renin production, the ability to reduce angiotensin production, the ability to reduce aldosterone production, the ability to reduce abnormally elevated cardiac filling pressures, the ability to optimize renal blood flow, or a combination thereof. In some cases, a polypeptide provided herein can increase endogenous ANP, BNP, and CNP levels. In some cases, a polypeptide provided herein can lack the ability to lower blood pressure and cause systemic hypotension. In some cases, a polypeptide provided herein can be an agonist for natriuretic peptide receptor-A, natriuretic peptide receptor-B, or both natriuretic peptide receptor-A and natriuretic peptide receptor-B.

A polypeptide provided herein can have any sequence and can have any length. For example, a polypeptide provided herein can include the sequence set forth in SEQ ID NO:1, SEQ ID NO:2, and SEQ ID NO:3. In some cases, a polypeptide provided herein can contain an amino acid sequence that aligns to (a) the sequence set forth in SEQ ID NO:1 with three or less (e.g., two or less, one, or zero) amino acid additions, deletions, substitutions, or combinations thereof, (b) the sequence set forth in SEQ ID NO:2 with five or less (e.g., four or less, three or less, two or less, one, or zero) amino acid additions, deletions, substitutions, or combinations thereof and (c) the sequence set forth in SEQ ID NO:3 with three or less (e.g., two or less, one, or zero) amino acid additions, deletions, substitutions, or combinations thereof. For example, a polypeptide provided herein can contain the sequence set forth in SEQ ID NO:1 with the exception that the first threonine residue or the last serine residue of SEQ ID NO:1 is deleted or replaced with a different amino acid residue.

Amino acid substitutions can be conservative amino acid substitutions. Conservative amino acid substitutions can be, for example, aspartic-glutamic as acidic amino acids; lysine/arginine/histidine as basic amino acids; leucine/isoleucine, methionine/valine, alanine/valine as hydrophobic amino acids; serine/glycine/alanine/threonine as hydrophilic amino acids. Conservative amino acid substitutions also include groupings based on side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. After making an amino acid substitution, the activities of the polypeptide containing the amino acid substitution can be assessed using the assays described herein.

In some cases, a polypeptide provided herein can contain (a) a first amino acid sequence that either is set forth in SEQ ID NO:1 or aligns to the sequence set forth in SEQ ID NO:1 with three or less (e.g., two or less, one, or zero) amino acid deletions, substitutions, or combinations thereof, (b) a second amino acid sequence that either is set forth in SEQ ID NO:2 or aligns to the sequence set forth in SEQ ID NO:2 with five or less (e.g., four or less, three or less, two or less, one, or zero) amino acid additions, substitutions, or combinations thereof, and (a) a third amino acid sequence that either is set forth in SEQ ID NO:3 or aligns to the sequence set forth in SEQ ID NO:3 with three or less (e.g., two or less, one, or zero) amino acid deletions, substitutions, or combinations thereof. For example, a polypeptide provided herein can comprise or consist of the sequence set forth in SEQ ID NO:4.

A polypeptide provided herein can have any length. For example, a polypeptide provided herein can be between 25 and 45 (e.g., between 26 and 44, between 27 and 43, between 28 and 42, between 29 and 41, between 30 and 40, between 31 and 39, or between 30 and 35) amino acid residues in length. It will be appreciated that a polypeptide with a length of 25 or 45 amino acid residues is a polypeptide with a length between 25 and 45 amino acid residues.

In some cases, a polypeptide provided herein can be a substantially pure polypeptide. As used herein, the term "substantially pure" with reference to a polypeptide means that the polypeptide is substantially free of other polypeptides, lipids, carbohydrates, and nucleic acid with which it is naturally associated. Thus, a substantially pure polypeptide is any polypeptide that is removed from its natural environment and is at least 60 percent pure or is any chemically synthesized polypeptide. A substantially pure polypeptide can be at least about 60, 65, 70, 75, 80, 85, 90, 95, or 99 percent pure. Typically, a substantially pure polypeptide will yield a single major band on a non-reducing polyacrylamide gel.

A polypeptide provide herein can be obtained by expression of a recombinant nucleic acid encoding the polypeptide or by chemical synthesis (e.g., using solid phase polypeptide synthesis methods or an peptide synthesizer such as an ABI 431A Peptide Synthesizer; Applied Biosystems; Foster City, Calif.). For example, standard recombinant technology using expression vectors encoding a polypeptide provide herein can be used. The resulting polypeptides then can be purified using, for example, affinity chromatographic techniques and HPLC. The extent of purification can be measured by any appropriate method, including but not limited to: column chromatography, polyacrylamide gel electrophoresis, or high-performance liquid chromatography. A polypeptide provide herein can be designed or engineered to contain a tag sequence that allows the polypeptide to be purified (e.g., captured onto an affinity matrix). For example, a tag such as c-myc, hemagglutinin, polyhistidine, or Flag™ tag (Kodak) can be used to aid polypeptide purification. Such tags can be inserted anywhere within the polypeptide including at either the carboxyl or amino termini. Other fusions that can be used include enzymes that aid in the detection of the polypeptide, such as alkaline phosphatase.

A polypeptide provided herein can be produced to contain three regions, a first region that includes an N-terminus (e.g., an N-terminus sequence from a human urodilatin polypeptide), a second region that includes a ring structure of a mature natriuretic polypeptide such as a human CNP polypeptide, and third region that includes a C-terminus (e.g., a C-terminus sequence from a human urodilatin polypeptide).

A polypeptide provided herein can be used to treat cardiovascular diseases, congestive heart failure, myocardial infarction, coronary artery diseases, renal diseases, hepatic diseases, cancer, metabolic diseases, or combinations thereof. For example, a CU-NP polypeptide having the amino acid sequence set forth in SEQ ID NO:4 can be administered to a human having coronary artery disease under conditions wherein the severity of the human's coronary artery disease symptoms is reduced.

A polypeptide provided herein can be formulated as a pharmaceutical composition by admixture with pharmaceutically acceptable non-toxic excipients or carriers. Such compositions can be administered to a subject in need thereof in an amount effective to treat, for example, heart, liver, kidney, or other sodium retaining conditions. Pharmaceutical compositions can be prepared for parenteral administration, particularly in the form of liquid solutions or suspensions in aqueous physiological buffer solutions; for oral administration, particularly in the form of tablets or capsules; or for intranasal administration, particularly in the form of powders, nasal drops, or aerosols. Compositions for other routes of administration can be prepared as desired using appropriate methods.

Formulations for parenteral administration can include as common excipients, sterile water, saline, polyalkylene glycols such as polyethylene glycol, oils of vegetable origin, hydrogenated naphthalenes, and combinations thereof. In some cases, biocompatible, biodegradable lactide polymer, lactide/glycolide copolymer, polyoxethylene-polyoxypropylene copolymers, or combinations thereof can be used as excipients for controlling the release of the polypeptide in vivo. Other suitable parenteral delivery systems that can be used include, without limitation, ethylene-vinyl acetate copolymer particles, osmotic pumps, implantable infusion systems, liposomes, and combinations thereof. Formulations for inhalation administration can include excipients such as lactose. Inhalation formulations can be aqueous solutions containing, for example, polyoxyethylene-9-lauryl ether, glycocholate, deoxycholate, or combinations thereof, or they can be oily solutions for administration in the form of nasal drops. If desired, a composition containing a polypeptide provided herein can be formulated as gel to be applied intranasally. Formulations for parenteral administration can include glycocholate for buccal administration.

For oral administration, tablets or capsules can be prepared using appropriate methods with pharmaceutically acceptable excipients such as binding agents (e.g., pregelatinized maize starch, polyvinylpyrrolidone, or hydroxypropyl methylcellulose); fillers (e.g., lactose, microcrystalline cellulose or calcium hydrogen phosphate); lubricants (e.g. magnesium stearate, talc or silica); disintegrants (e.g., potato starch or sodium starch glycolate); or wetting agents (e.g., sodium lauryl sulfate). Tablets can be coated using appropriate methods. Preparations for oral administration can be formulated to give controlled release of the polypeptide.

Nasal preparations can be presented in a liquid form or as a dry product. Nebulised aqueous suspensions or solutions can include carriers or excipients to adjust pH and/or tonicity.

Nucleic Acids Encoding Polypeptides

This document also provides isolated nucleic acids that encode one or more of the polypeptides provided herein. The term "isolated" as used herein with reference to nucleic acid refers to a naturally-occurring nucleic acid that is not immediately contiguous with both of the sequences with which it is immediately contiguous (one on the 5' end and one on the 3' end) in the naturally-occurring genome of the organism from which it is derived. For example, an isolated nucleic acid can be, without limitation, a recombinant DNA molecule of any length, provided one of the nucleic acid sequences normally found immediately flanking that recombinant DNA molecule in a naturally-occurring genome is removed or absent. Thus, an isolated nucleic acid includes, without limitation, a recombinant DNA that exists as a separate molecule (e.g., a cDNA or a genomic DNA fragment produced by PCR or restriction endonuclease treatment) independent of other sequences as well as recombinant DNA that is incorporated into a vector, an autonomously replicating plasmid, a virus (e.g., a retrovirus, adenovirus, or herpes virus), or into the genomic DNA of a prokaryote or eukaryote. In addition, an isolated nucleic acid can include a recombinant DNA molecule that is part of a hybrid or fusion nucleic acid sequence.

The term "isolated" as used herein with reference to nucleic acid also includes any non-naturally-occurring nucleic acid since non-naturally-occurring nucleic acid sequences are not found in nature and do not have immediately contiguous sequences in a naturally-occurring genome. For example, non-naturally-occurring nucleic acid such as an engineered nucleic acid is considered to be isolated nucleic acid. Engineered nucleic acid (e.g., a nucleic acid encoding a polypeptide comprising or consisting of the amino acid sequence set forth in SEQ ID NO:4) can be made using common molecular cloning or chemical nucleic acid synthesis techniques. Isolated non-naturally-occurring nucleic acid can be independent of other sequences, or incorporated into a vector, an autonomously replicating plasmid, a virus (e.g., a retrovirus, adenovirus, or herpes virus), or the genomic DNA of a prokaryote or eukaryote. In addition, a non-naturallyoccurring nucleic acid can include a nucleic acid molecule that is part of a hybrid or fusion nucleic acid sequence. A nucleic acid existing among hundreds to millions of other nucleic acids within, for example, cDNA libraries or genomic libraries, or gel slices containing a genomic DNA restriction digest, is not to be considered an isolated nucleic acid.

As used herein, the term "nucleic acid" refers to both RNA and DNA, including mRNA, cDNA, genomic DNA, synthetic (e.g., chemically synthesized) DNA, and nucleic acid analogs. The nucleic acid can be double-stranded or single-stranded, and where single-stranded, can be the sense strand or the antisense strand. In addition, nucleic acid can be circular or linear. Nucleic acid analogs can be modified at the base moiety, sugar moiety, or phosphate backbone to improve, for example, stability, hybridization, or solubility of a nucleic acid. Modifications at the base moiety include deoxyuridine for deoxythymidine, and 5-methyl-2'-deoxycytidine and 5-bromo-2'-deoxycytidine for deoxycytidine. Modifications of the sugar moiety can include modification of the 2' hydroxyl of the ribose sugar to form 2'-O-methyl or 2'-O-allyl sugars. The deoxyribose phosphate backbone can be modified to produce morpholino nucleic acids, in which each base moiety is linked to a six-membered, morpholino ring, or peptide nucleic acids, in which the deoxyphosphate backbone is replaced by a pseudopeptide backbone and the four bases are retained. See, for example, Summerton and Weller *Antisense Nucleic Acid Drug Dev.*, 7:187-195 (1997); and Hyrup et al. *Bioorgan. Med. Chem.*, 4:5-23 (1996). In addition, the deoxyphosphate backbone can be replaced with, for example, a phosphorothioate or phosphorodithioate backbone, a phosphoroamidite, or an alkyl phosphotriester backbone.

A nucleic acid provided herein can comprise or consist of a sequence that encodes the amino acid sequence set forth in SEQ ID NO:4. For example, such a nucleic acid can contain the human nucleic acid sequence for CNP and urodilatin engineered to encode the amino acid sequence set forth in SEQ ID NO:4.

Typically, an isolated nucleic acid provided herein is at least 10 nucleotides in length (e.g., 10, 15, 20, 25, 30, 35, 40, 50, 75, 100, 200, 300, 350, 400, or more nucleotides in length). Nucleic acid molecules that are less than full-length can be useful, for example, as primers or probes for diagnostic purposes. Isolated nucleic acid molecules can be produced by standard techniques, including, without limitation, common molecular cloning and chemical nucleic acid synthesis techniques. For example, polymerase chain reaction (PCR) techniques can be used. PCR refers to a procedure or technique in which target nucleic acids are enzymatically amplified. Sequence information from the ends of the region of interest or beyond typically is employed to design oligonucleotide primers that are identical in sequence to opposite strands of the template to be amplified. PCR can be used to amplify specific sequences from DNA as well as RNA, including sequences from total genomic DNA or total cellular RNA. Primers typically are 15 to 50 nucleotides in length, but can range from 10 nucleotides to hundreds of nucleotides in length. For example, a primer can be 12, 15, 16, 17, 18, 19, 20, 21, 22, 23, 24, 25, 26, 27, 28, 29, 30, 35, 40, or 45 nucleotides in length. A primer can be purified from a restriction digest by conventional methods, or can be chemically synthesized. Primers typically are single-stranded for maximum efficiency in amplification, but a primer can be double-stranded. Double-stranded primers are first denatured (e.g., treated with heat) to separate the strands before use in amplification. General PCR techniques are described, for example in *PCR Primer: A Laboratory Manual*, ed. by Dieffenbach and Dveksler, Cold Spring Harbor Laboratory Press, 1995. When using RNA as a source of template, reverse transcriptase can be used to synthesize a complementary DNA (cDNA) strand. Ligase chain reaction, strand displacement amplification, self-sustained sequence replication or nucleic acid sequence-based amplification also can be used to obtain isolated nucleic acids as described elsewhere (Lewis, *Genetic Engineering News*, 12(9):1 (1992); Guatelli et al., *Proc. Natl. Acad. Sci. USA*, 87:1874-1878 (1990); and Weiss, *Science*, 254:1292 (1991)).

Isolated nucleic acids also can be chemically synthesized, either as a single nucleic acid molecule (e.g., using automated DNA synthesis in the 3' to 5' direction using phosphoramidite technology) or as a series of oligonucleotides. For example, one or more pairs of long oligonucleotides (e.g., >100 nucleotides) can be synthesized that contain the desired sequence, with each pair containing a short segment of complementarity (e.g., about 15 nucleotides) such that a duplex is formed when the oligonucleotide pair is annealed. DNA polymerase is used to extend the oligonucleotides, resulting in a single, double-stranded nucleic acid molecule per oligonucleotide pair, which then can be ligated into a vector.

Isolated nucleic acids also can be obtained by mutagenesis. For example, a nucleic acid sequence encoding a polypeptide having the sequence set forth in SEQ ID NO:1, 2, 3, or 4 can be mutated using standard techniques such as, for example, oligonucleotide-directed mutagenesis and/or site-directed mutagenesis through PCR. See, *Short Protocols in Molecular Biology*, Chapter 8, Green Publishing Associates and John Wiley & Sons, Edited by Ausubel et al., 1992. Such mutations include additions, deletions, substitutions, and combinations thereof.

Vectors and Host Cells

This document also provides vectors containing a nucleic acid provided herein. As used herein, a "vector" is a replicon, such as a plasmid, phage, or cosmid, into which another DNA segment can be inserted so as to bring about the replication of the inserted segment. A vector can be an expression vector. An "expression vector" is a vector that includes one or more expression control sequences, and an "expression control sequence" is a DNA sequence that controls and regulates the transcription and/or translation of another DNA sequence.

In an expression vector provided herein, the nucleic acid can be operably linked to one or more expression control sequences. As used herein, "operably linked" means incorporated into a genetic construct so that expression control sequences effectively control expression of a coding sequence of interest. Examples of expression control sequences include promoters, enhancers, and transcription terminating regions. A promoter is an expression control sequence composed of a region of a DNA molecule, typically within 100 nucleotides upstream of the point at which transcription starts (generally near the initiation site for RNA polymerase II). To bring a coding sequence under the control of a promoter, it can be necessary to position the translation initiation site of the translational reading frame of the polypeptide between one and about fifty nucleotides downstream of the promoter. Enhancers provide expression specificity in terms of time, location, and level. Unlike promoters, enhancers can function when located at various distances from the transcription site. An enhancer also can be located downstream from the transcription initiation site. A coding sequence is "operably linked" and "under the control" of expression control sequences in a cell when RNA polymerase is able to transcribe the coding sequence into mRNA, which then can be translated into the polypeptide encoded by the coding sequence.

Suitable expression vectors include, without limitation, plasmids and viral vectors derived from, for example, bacteriophage, baculoviruses, tobacco mosaic virus, herpes viruses, cytomegalovirus, retroviruses, poxviruses, adenoviruses, and adeno-associated viruses. Numerous vectors and expression systems are commercially available from such corporations as Novagen (Madison, Wis.), Clontech Laboratories (Mountain View, Calif.), Stratagene (La Jolla, Calif.), and Invitrogen/Life Technologies (Carlsbad, Calif.).

An expression vector can include a tag sequence designed to facilitate subsequent manipulation of the expressed nucleic acid sequence (e.g., purification or localization). Tag sequences, such as green fluorescent protein (GFP), glutathione S-transferase (GST), polyhistidine, c-myc, hemagglutinin, or Flag™ tag (Kodak, New Haven, Conn.) sequences typically are expressed as a fusion with the encoded polypeptide. Such tags can be inserted anywhere within the polypeptide including at either the carboxyl or amino terminus.

This document also provides host cells containing a nucleic acid molecule and/or nucleic acid vector provided herein. The term "host cell" refers to prokaryotic cells and eukaryotic cells into which a nucleic acid molecule or vector can be introduced. Any method can be used to introduce nucleic acid into a cell. For example, calcium phosphate precipitation, electroporation, heat shock, lipofection, microinjection, and viral-mediated nucleic acid transfer can be used introduce nucleic acid into cells. In addition, naked DNA can be delivered directly to cells in vivo as described elsewhere (U.S. Pat. Nos. 5,580,859 and 5,589,466).

Detecting Polypeptides

This document provides methods and materials for detecting a polypeptide provided herein. Such methods and materials can be used to monitor polypeptide levels within a mammal receiving the polypeptide as a therapeutic. A polypeptide provided herein (e.g., a CU-NP polypeptide having the amino acid sequence set forth in SEQ ID NO:4) can be detected, for example, immunologically using one or more antibodies. As used herein, the term "antibody" includes intact molecules as well as fragments thereof that are capable of binding to an epitopic determinant of a polypeptide provided herein. The term "epitope" refers to an antigenic determinant on an antigen to which the paratope of an antibody binds. Epitopic determinants usually consist of chemically active surface groupings of molecules such as amino acids or sugar side chains, and typically have specific three-dimensional structural characteristics, as well as specific charge characteristics. Epitopes generally have at least five contiguous amino acids (a continuous epitope), or alternatively can be a set of non-contiguous amino acids that define a particular structure (e.g., a conformational epitope). The term "antibody" includes polyclonal antibodies, monoclonal antibodies, humanized or chimeric antibodies, single chain Fv antibody fragments, Fab fragments, and F(ab)$_2$ fragments. Polyclonal antibodies are heterogenous populations of antibody molecules that are contained in the sera of the immunized animals. Monoclonal antibodies are homogeneous populations of antibodies to a particular epitope of an antigen.

Antibody fragments that have specific binding affinity for a polypeptide provided herein (e.g., a CU-NP polypeptide having the amino acid sequence set forth in SEQ ID NO:4) can be generated by known techniques. For example, F(ab')2 fragments can be produced by pepsin digestion of the antibody molecule; Fab fragments can be generated by reducing the disulfide bridges of F(ab')2 fragments. In some cases, Fab expression libraries can be constructed. See, for example, Huse et al., Science, 246:1275 (1989). Once produced, antibodies or fragments thereof can be tested for recognition of a polypeptide provided herein by standard immunoassay methods including ELISA techniques, radioimmunoassays, and Western blotting. See, Short Protocols in Molecular Biology, Chapter 11, Green Publishing Associates and John Wiley & Sons, Edited by Ausubel, F. M et al., 1992.

In immunological assays, an antibody having specific binding affinity for a polypeptide provided herein or a secondary antibody that binds to such an antibody can be labeled, either directly or indirectly. Suitable labels include, without limitation, radionuclides (e.g., $^{125}$I, $^{131}$I, $^{35}$S, $^{3}$H, $^{32}$P, $^{33}$P, or $^{14}$C), fluorescent moieties (e.g., fluorescein, FITC, PerCP, rhodamine, or PE), luminescent moieties (e.g., Qdot™ nanoparticles supplied by Invitrogen (Carlsbad, Calif.)), compounds that absorb light of a defined wavelength, or enzymes (e.g., alkaline phosphatase or horseradish peroxidase). Antibodies can be indirectly labeled by conjugation with biotin then detected with avidin or streptavidin labeled with a molecule described above. Methods of detecting or quantifying a label depend on the nature of the label and are known in the art. Examples of detectors include, without limitation, x-ray film, radioactivity counters, scintillation counters, spectrophotometers, colorimeters, fluorometers, luminometers, and densitometers. Combinations of these approaches (including "multi-layer" assays) familiar to those in the art can be used to enhance the sensitivity of assays.

Immunological assays for detecting a polypeptide provided herein can be performed in a variety of known formats, including sandwich assays, competition assays (competitive RIA), or bridge immunoassays. See, for example, U.S. Pat. Nos. 5,296,347; 4,233,402; 4,098,876; and 4,034,074. Methods of detecting a polypeptide provided herein generally include contacting a biological sample with an antibody that binds to a polypeptide provided herein and detecting binding of the polypeptide to the antibody. For example, an antibody having specific binding affinity for a polypeptide provided herein can be immobilized on a solid substrate by any of a variety of methods known in the art and then exposed to the biological sample. Binding of the polypeptide to the antibody on the solid substrate can be detected by exploiting the phenomenon of surface plasmon resonance, which results in a change in the intensity of surface plasmon resonance upon binding that can be detected qualitatively or quantitatively by an appropriate instrument, e.g., a Biacore apparatus (Biacore International AB, Rapsgatan, Sweden). In some cases, the antibody can be labeled and detected as described above. A standard curve using known quantities of a polypeptide provided herein can be generated to aid in the quantitation of the levels of the polypeptide.

In some embodiments, a "sandwich" assay in which a capture antibody is immobilized on a solid substrate can be used to detect the presence, absence, or level of a polypeptide provided herein. The solid substrate can be contacted with the biological sample such that any polypeptide of interest in the sample can bind to the immobilized antibody. The presence, absence, or level of the polypeptide bound to the antibody can be determined using a "detection" antibody having specific binding affinity for the polypeptide. In some embodiments, a capture antibody can be used that has binding affinity for CNP or urodilatin as well as a polypeptide provided herein. In this embodiment, a detection antibody can be used that has specific binding affinity for a particular polypeptide provided herein (e.g., a CU-NP polypeptide having the amino acid sequence set forth in SEQ ID NO:4). It is understood that in sandwich assays, the capture antibody should not bind to the same epitope (or range of epitopes in the case of a polyclonal antibody) as the detection antibody. Thus, if a monoclonal antibody is used as a capture antibody, the detection antibody can be another monoclonal antibody that binds to an epitope that is either physically separated from or only partially overlaps with the epitope to which the capture monoclonal antibody binds, or a polyclonal antibody that binds to epitopes other than or in addition to that to which the capture monoclonal antibody binds. If a polyclonal antibody is used as a capture antibody, the detection antibody can be either a monoclonal antibody that binds to an epitope that is either physically separated from or partially overlaps with any of the epitopes to which the capture polyclonal antibody binds, or a polyclonal antibody that binds to epitopes other than or in addition to that to which the capture polyclonal antibody binds. Sandwich assays can be performed as sandwich ELISA assays, sandwich Western blotting assays, or sandwich immunomagnetic detection assays.

Suitable solid substrates to which an antibody (e.g., a capture antibody) can be bound include, without limitation, microtiter plates, tubes, membranes such as nylon or nitrocellulose membranes, and beads or particles (e.g., agarose, cellulose, glass, polystyrene, polyacrylamide, magnetic, or magnetizable beads or particles). Magnetic or magnetizable particles can be particularly useful when an automated immunoassay system is used.

Antibodies having specific binding affinity for a polypeptide provided herein can be produced through standard methods. For example, a polypeptide can be recombinantly produced as described above, can be purified from a biological sample (e.g., a heterologous expression system), or can be chemically synthesized, and used to immunize host animals, including rabbits, chickens, mice, guinea pigs, or rats. For example, a polypeptide having the amino acid sequence set forth in SEQ ID NO:4, or fragments thereof that are at least six amino acids in length, can be used to immunize an animal. Various adjuvants that can be used to increase the immunological response depend on the host species and include Freund's adjuvant (complete and incomplete), mineral gels such as aluminum hydroxide, surface active substances such as lysolecithin, pluronic polyols, polyanions, peptides, oil emulsions, keyhole limpet hemocyanin and dinitrophenol. Monoclonal antibodies can be prepared using a polypeptide provided herein and standard hybridoma technology. In particular, monoclonal antibodies can be obtained by any technique that provides for the production of antibody molecules by continuous cell lines in culture such as described by Kohler et al., Nature, 256:495 (1975), the human B-cell hybridoma technique (Kosbor et al., Immunology Today, 4:72 (1983); Cole et al., Proc. Natl. Acad. Sci. USA, 80:2026 (1983)), and the EBV-hybridoma technique (Cole et al., "Monoclonal Antibodies and Cancer Therapy," Alan R. Liss, Inc., pp. 77-96 (1983)). Such antibodies can be of any immunoglobulin class including IgG, IgM, IgE, IgA, IgD, and any subclass thereof. The hybridoma producing the monoclonal antibodies can be cultivated in vitro and in vivo.

Other techniques for detecting a polypeptide provided herein include mass-spectrophotometric techniques such as electrospray ionization (ESI), and matrix-assisted laser desorption-ionization (MALDI). See, for example, Gevaert et al., *Electrophoresis*, 22(9):1645-51 (2001); Chaurand et al., *J. Am. Soc. Mass Spectrom.*, 10(2):91-103 (1999). Mass spectrometers useful for such applications are available from Applied Biosystems (Foster City, Calif.); Bruker Daltronics (Billerica, Mass.); and Amersham Pharmacia (Sunnyvale, Calif.).

The invention will be further described in the following examples, which do not limit the scope of the invention described in the claims.

EXAMPLES

Example 1

Synthesis of CU-NP

Figure 1:
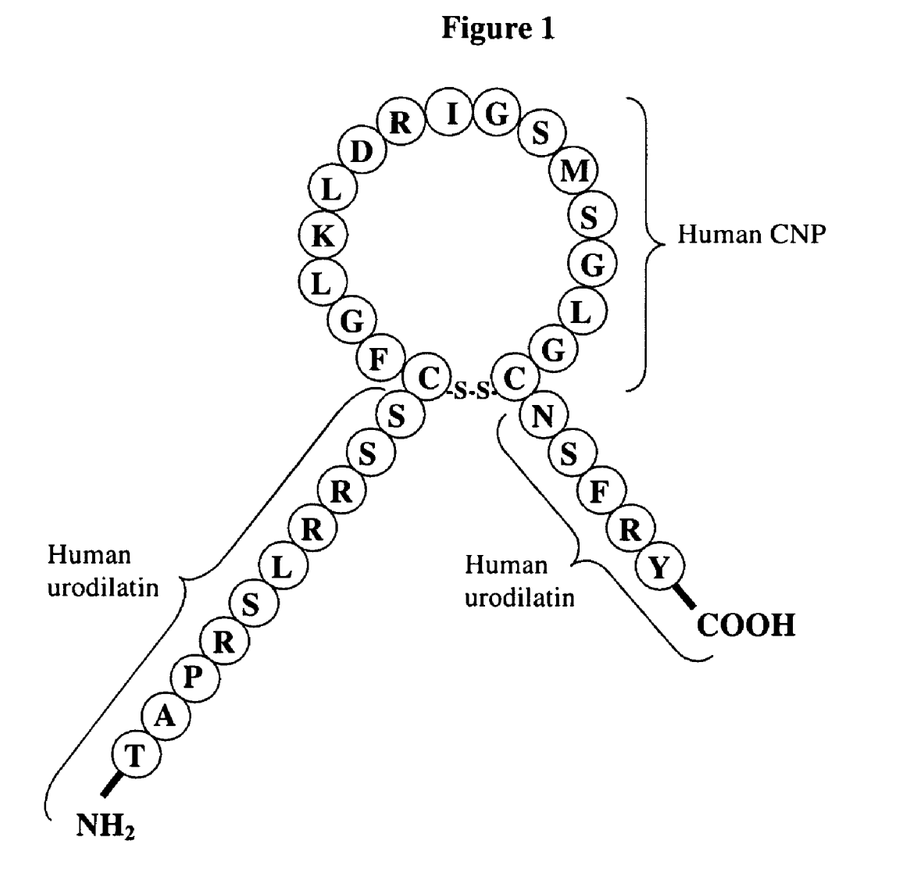
FIG. 1 is a schematic diagram of a CU-NP polypeptide that is 32 amino acid residues in length (SEQ ID NO:4). The first ten amino acid residues of SEQ ID NO:4 correspond to amino acid residues 1 to 10 of human urodilatin and are designated as SEQ ID NO:1. Amino acid residues 11 to 27 of SEQ ID NO:4 correspond to amino acid residues 6 to 22 of human mature CNP and are designated as SEQ ID NO:2. Amino acid residues 28 to 32 of SEQ ID NO:4 correspond to amino acid residues 28 to 32 of human urodilatin and are designated as SEQ ID NO:3.

A polypeptide with the sequence set forth in FIG. 1 was designed and synthesized using an ABI 431A Peptide Synthesizer. This polypeptide is referred to as a CU-NP polypeptide (FIG. 1). The synthesized CU-NP polypeptide was confirmed by high-performance liquid chromatography/mass spectrometry. Its molecular weight is 3535.09, and its amino acid sequence is Thr-Ala-Pro-Arg-Ser-Leu-Arg-Arg-Ser-Ser-Cys-Phe-Gly-Leu-Lys-Leu-Asp-Arg-Ile-Gly-Ser-Met-Ser-Gly-Leu-Gly-Cys-Asn-Ser-Phe-Arg-Tyr (SEQ ID NO:4) with a disulfide bridge joining the Cys residues (FIG. 1).

Example 2

In Vivo Effects of CU-NP

Cardiorenal function was assessed in three normal anesthetized dogs. Clearances were obtained at pre-infusion, during intravenous infusion of 10, 50, and 100 ng CU-NP/kg/minute for 45 minutes at each dosage level (i.e., each dog received consecutive 45-minute infusions of 10, 50, and 100 ng/kg/minute), and post-infusion. Tubular $Na^+$ reabsorption and GFR were assessed by clearance of $Li^+$ and inulin, respectively. Neurohormones were quantified by radioimmunoassays. Data were analyzed by repeated measures ANOVA followed by Dunnett's test. The results (mean±SEM) are presented in Table 1.

In addition, plasma renin activity decreased from 9±2 to 5±1* to 3±1† to 3±1† ng/mL/hour, and angiotensin II levels decreased from 18±1 to 10±0.4† to 5±0.4† to 7±1† pg/mL. No significant change in QTc interval (ms) was observed at the end of infusion at 100 ng/kg/minute (329±15) versus pre-infusion (323±6).

These results demonstrate that a polypeptide containing CNP and urodilatin amino acid sequences can, in a dose dependent manner, (1) increase natriuresis, diuresis, and GFR, (2) decrease cardiac filling pressures, and (3) inhibit renin and angiotensin, without inducing significant hypotension.

TABLE 1

Renal and cardiovascular data for CU-NP

| | Pre-Infusion | 10 ng/kg/minute | 50 ng/kg/minute | 100 ng/kg/minute | Post-Infusion |
|---|---|---|---|---|---|
| GFR (mL/min) | 31 ± 5 | 39 ± 1 | 43 ± 4* | 53 ± 3† | 36 ± 2 |
| Urine flow (mL/min) | 0.09 ± 0.01 | 0.3 ± 0.07 | 1.5 ± 0.5† | 1.9 ± 0.3† | 0.3 ± 0.05 |

TABLE 1-continued

Renal and cardiovascular data for CU-NP

|  | Pre-Infusion | 10 ng/kg/minute | 50 ng/kg/minute | 100 ng/kg/minute | Post-Infusion |
|---|---|---|---|---|---|
| Na$^+$ excretion (μEq/min) | 1.9 ± 0.9 | 33 ± 13 | 235 ± 72† | 342 ± 60† | 66 ± 12 |
| PFR$_{Na+}$ (%) | 92 ± 0.9 | 73 ± 4.5† | 54 ± 1.8† | 55 ± 2.6† | 62 ± 3.5† |
| DFR$_{Na+}$ (%) | 99 ± 0.3 | 98 ± 0.5 | 92 ± 1.6† | 90 ± 0.8† | 97 ± 0.6* |
| Renal cGMP generation (pmol/min) | 356 ± 36 | 534 ± 94 | 1301 ± 60* | 4608 ± 370† | 1086 ± 27 |
| PCWP (mmHg) | 4.6 ± 0.7 | 3.8 ± 1 | 2.5 ± 1† | 1.7 ± 0.9† | 3.2 ± 1* |
| RAP (mmHg) | 1.5 ± 1 | 0.9 ± 0.9 | 0.6 ± 1* | −0.2 ± 0.8† | 0.1 ± 0.9† |
| MAP (mmHg) | 129 ± 17 | 129 ± 13 | 128 ± 10 | 120 ± 11 | 124 ± 13 |

*= P < 0.05;
†= P < 0.01;
GFR = glomerular filtration rate; PFRNa$^+$ = proximal fractional reabsorption of sodium; DFRNa$^+$ = distal fractional reabsorption of sodium; PCWP = pulmonary capillary wedge pressure; RAP = right atrial pressure; MAP = mean arterial pressure.

Example 3

Further Biological Effects of CU-NP

CU-NP or CNP polypeptide was intravenously infused into normal anesthetized dogs at 50 ng/kg/minute for 75 minutes. Blood and urine samples were collected pre-infusion (pre-I), at 30 and 60 minutes of infusion, and post-infusion (post-I). Inulin clearance was used for assessment of glomerular filtration rate (GFR). The lithium clearance technique was used for measurement of proximal and distal fractional reabsorption of Na$^+$ (PFR$_{Na}$ and DFR$_{Na}$, respectively). Comparisons at the latter three time points versus pre-I were made. Student's t-test was used when comparing results for two time points, whereas repeated measures ANOVA was used to compare four time points. Results (mean±SEM) are presented in Tables 2A and 2B.

The CU-NP polypeptide significantly increased plasma cGMP and urinary cGMP excretion. CU-NP also increased urine flow and urinary Na+ excretion, and led to enhanced glomerular filtration rate. Pulmonary capillary wedge pressure and right atrial pressure were reduced without reducing systemic hypotension. Pulmonary arterial pressure also was significantly reduced, and cardiac output was preserved.

Plasma renin activity, angiotensin II levels, and aldosterone levels were suppressed during CU-NP infusion, but were followed by an elevation or 'rebound' following cessation of CU-NP infusion. These data suggest that a long-acting form of CU-NP can be used for continued suppression of neurohormones.

CU-NP also significantly increased renal generation of cGMP and urinary K$^+$ excretion. Both PFR$_{Na+}$ and DFR$_{Na+}$ were significantly reduced. These findings were associated with an increase in weight-adjusted renal blood flow and a reduction in renal vascular resistance. An increase in hematocrit also was observed. Plasma ANP, plasma BNP, and plasma CNP were increased, as was urinary excretion of ANP, BNP, and CNP.

These results demonstrate that a CU-NP polypeptide can have cGMP-activating, diuretic, natriuretic, GFR-enhancing, renin-angiotensin-aldosterone system (RAAS)-suppressing, cardiac-unloading, and favorable renal hemodynamic activities while lacking the ability to lower blood pressure and cause systemic hypotension. In addition, these results demonstrate that a CU-NP polypeptide can increase endogenous ANP and BNP levels. The tubular effects of the synthesized CU-NP polypeptide are consistent with actions at the level of proximal tubule and inner medullary collecting duct cells.

TABLE 2A

Renal and cardiovascular data for CU-NP

|  | Pre-Infusion | 30 minutes | 60 minutes | Post-Infusion |
|---|---|---|---|---|
| GFR (mL/min) | 38.4 ± 3.6 | 50.7 ± 2.6* | 53.8 ± 2.8†‡ | 50.1 ± 3.5* |
| Urine flow (mL/min) | 0.13 ± 0.02 | 1.28 ± 0.25†¶ | 1.34 ± 0.22†¶ | 0.33 ± 0.04 |
| Na$^+$ excretion (μEq/min) | 8.0 ± 3.3 | 216.4 ± 42.3†¶ | 237.7 ± 35.8†¶ | 51.2 ± 9.4 |
| K$^+$ excretion (μeq/min) | 14.9 ± 4.5 | 68.3 ± 12.5† | 74.6 ± 15.3† | 32.9 ± 3.0 |
| PFR$_{Na+}$ (%) | 84.9 ± 2.5 | 62.4 ± 4.0† | 61.3 ± 1.9† | 70.4 ± 2.8† |
| DFR$_{Na+}$ (%) | 99.2 ± 0.2 | 92.4 ± 1.2†¶ | 92.2 ± 1.1†¶ | 97.7 ± 0.4 |
| Renal generation of cGMP (pmol/min) | 469.0 ± 55.4 | 2168 ± 531†§ | 2987 ± 622†¶ | 1394 ± 185 |
| Plasma cGMP (pmol/mL) | 8.2 ± 0.7 | 26.2 ± 1.3†¶ | 29.8 ± 1.5†¶ | 13.0 ± 0.9† |
| Urinary cGMP excretion (pmol/min) | 770 ± 48 | 3508 ± 574†¶ | 4591 ± 664†¶ | 2052 ± 208 |
| PCWP (mmHg) | 5.6 ± 0.9 | 3.9 ± 0.7* | 2.9 ± 0.9† | 4.3 ± 0.8 |
| RAP (mmHg) | 1.1 ± 0.6 | 0.3 ± 0.5 | −0.1 ± 0.5* | 0.7 ± 0.4 |
| Systemic hypotension (mmHg) | 135.9 ± 3.9 | 135.9 ± 2.7 | 133.9 ± 3.6 | 142.3 ± 2.7† |
| PAP (mmHg) | 11.8 ± 0.9 | 10.7 ± 0.8* | 10.5 ± 0.7† | 12.3 ± 0.7 |
| Cardiac output (L/min) | 3.1 ± 0.3 | 3.4 ± 0.5 | 3.0 ± 0.5 | 2.8 ± 0.5 |

TABLE 2A-continued

Renal and cardiovascular data for CU-NP

|  | Pre-Infusion | 30 minutes | 60 minutes | Post-Infusion |
|---|---|---|---|---|
| Plasma renin activity (ng/mL/hour) | 8.8 ± 2 | 2.5 ± 0.8† | 1.5 ± 0.4† | 14.0 ± 1.3† |
| Angiotensin II (pg/mL) | 13.9 ± 2.0 | 6.9 ± 0.7† | 4.5 ± 0.3† | 22.6 ± 1.6† |
| Aldosterone (ng/dL) | 15.8 ± 2.7 | 14.2 ± 2.2 | 12.1 ± 2.1 | 30.4 ± 3.5† |
| Adjusted RBF (mL/kg/min) | 10.8 ± 0.8 | 11.64 ± 0.5 | 12.21 ± 0.4† | 11.60 ± 0.5 |
| RVR (×10$^{-3}$ mmHg · min · L$^{-1}$) | 0.55 ± 0.05 | 0.50 ± 0.04 | 0.47 ± 0.03† | 0.53 ± 0.04 |
| Hematocrit (%) | 37.8 ± 1.3 | 40.3 ± 1.3† | 41.1 ± 1.4† | 40.3 ± 1.8† |
| Plasma ANP (pg/mL) | 14.1 ± 0.8 | 16.7 ± 0.9* | 16.6 ± 1.1* | 15.2 ± 0.6 |
| Plasma BNP (pg/mL) | 8.2 ± 0.9 | 21.0 ± 1.8† | 17.0 ± 2.2† | 10.1 ± 1.4 |
| Plasma CNP (pg/mL) | 4.0 ± 0.3 | 15.4 ± 0.9† | 15.1 ± 1.4† | 3.2 ± 0.2 |
| ANP excretion (pg/min) | 3.2 ± 1.5 | 21.9 ± 9.5 | 28.3 ± 13.6 | 10.4 ± 2.5 |
| BNP excretion (pg/min) | 13.9 ± 1.5 | 18.2 ± 1.5 | 19.3 ± 1.2 | 28.3 ± 5.4* |
| CNP excretion (pg/min) | 2.0 ± 0.4 | 4.0 ± 1.2 | 9.1 ± 3.9 | 21.5 ± 17.4 |

* = $P < 0.05$ vs. pre-I;
† = $P < 0.01$ vs. pre-I;
‡ = $P < 0.05$ vs. CNP;
§ = $P < 0.01$ vs. CNP;
¶ = $P < 0.001$ vs. CNP;
GFR = glomerular filtration rate; PFR$_{Na+}$ = proximal fractional reabsorption of sodium; DFR$_{Na+}$ = distal fractional reabsorption of sodium; PCWP = pulmonary capillary wedge pressure; RAP = right atrial pressure; PAP = pulmonary arterial pressure; RBF = renal blood flow; RVR = renal vascular resistance.

TABLE 2B

Comparative renal and cardiovascular data for CNP

|  | Pre-Infusion | 30 minutes | 60 minutes | Post-Infusion |
|---|---|---|---|---|
| GFR (mL/min) | 38 ± 4 | 42 ± 4 | 39 ± 3 | 44 ± 3 |
| Urine flow (mL/min) | 0.1 ± 0.02 | 0.3 ± 0.06† | 0.4 ± 0.02† | 0.3 ± 0.04 |
| Na$^+$ excretion (μEq/min) | 16 ± 6 | 56 ± 21 | 71 ± 8* | 30 ± 8 |
| PFR$_{Na+}$ (%) | 83 ± 3 | 67 ± 3 | 51 ± 7† | 68 ± 3* |
| DFR$_{Na+}$ (%) | 99 ± 0.5 | 98 ± 0.8 | 98 ± 0.5 | 99 ± 0.2 |
| Renal generation of cGMP (pmol/min) | 491 ± 65 | 452 ± 202 | 603 ± 199 | 582 ± 91 |
| Plasma cGMP (pmol/mL) | 8 ± 1 | 11 ± 1† | 12 ± 1† | 12 ± 1† |
| Urinary cGMP excretion (pmol/min) | 830 ± 74 | 1119 ± 102* | 1338 ± 81† | 1090 ± 76* |

* = $P < 0.05$ vs. pre-I;
† = $P < 0.01$ vs. pre-I;
GFR = glomerular filtration rate; PFR$_{Na+}$ = proximal fractional reabsorption of sodium; DFR$_{Na+}$ = distal fractional reabsorption of sodium.

Example 4

Evaluation of CU-NP in Human Aortic Endothelial Cells and In Vivo

CU-NP was tested in human aortic endothelial cells (HAEC), and the time course of cGMP activation in vivo was defined. CU-NP was incubated with HAEC (passages 2-5, at 80-90% confluency) at $10^{-10}$, $10^{-8}$ or $10^{-6}$ M for 10 minutes in a $CO_2$ incubator. CU-NP (n=6) or CNP (n=3) was intravenously infused into normal anesthetized dogs at 14 pmol/kg/min for 75 minutes. Blood was collected pre-infusion, at 25, 30, 45, 60, 75 minutes during infusion (I) and at 1, 2, 4, 6, 10, 20, 30, 45, 60 minutes post-infusion (post-I). Cyclic GMP was quantified by radioimmunoassay.

As shown in Table 3, CU-NP stimulated cGMP production in HAEC ($P<0.01$ for $10^{-6}$ M vs. no treatment). Further, CU-NP increased plasma cGMP in vivo vs. pre-I (all time points during I and post-I, $P<0.01$, except at 45 minutes post-I, $P<0.05$). CU-NP activated cGMP to a greater extent as compared to CNP ($P<0.001$, 25 minutes I through 30 minutes post-I). Thus, CU-NP significantly activated cGMP in HAEC, and also significantly stimulated cGMP to a greater extent than CNP in vivo.

TABLE 3

CU-NP effects on HAEC

| CU-NP Concentration | cGMP (mean ± SEM, pmol/mL) |
|---|---|
| $10^{-10}$ M | 0.0007 ± 0.0007 |
| $10^{-8}$ M | 0.03 ± 0.02 |
| $10^{-6}$ M | 0.571 ± 0.05† |
| No treatment | 0.003 ± 0.002 |

† = $P < 0.01$ vs. no treatment.

Example 5 cGMP Stimulating Actions of CU-NP in Isolated Canine Glomeruli

Experiments were conducted to determine whether CU-NP directly stimulates cGMP in isolated glomeruli, and to compare the cGMP-activating actions of CU-NP with CNP, URO, and CNP-C, which consisted of the full-length 22-AA of CNP with a duplicate of the N-terminus fused in the C-terminal position. Glomeruli were isolated upon harvest of normal canine kidneys. CU-NP, CNP, URO, and CNP-C ($10^{-5}$ M) were incubated with glomeruli vs. control. Cyclic GMP was measured by RIA, with correction for protein levels. CU-NP and URO elicited greater cGMP responses than respective controls ($P<0.01$), but without difference between groups. CU-NP and URO stimulated greater cGMP responses vs. CNP and vs. CNP-C ($P<0.001$). Thus, CU-NP stimulated cGMP in glomeruli to a greater extent than CNP, but to a similar extent as URO. CNP-C did not activate cGMP. These data suggest that enhanced cGMP potentially activated may require N- and/or C-termini of ligands for NP receptor-A.

TABLE 4

CU-NP effects on cGMP production in isolated glomeruli

| Treatment | cGMP (mean ± SEM; fmol/μg) |
|---|---|
| CU-NP | 0.73 ± 0.09[†‡] |
| CNP | 0.0019 ± 0.0005 |
| URO | 0.69 ± 0.07[†‡] |
| CNP-C | 0.00597 ± 0.0053 |

[†]= $P < 0.01$ vs. corresponding control;
[‡]= $P < 0.001$ vs. CNP and CNP-C.

Example 6

Hemoconcentrating Effects of CU-NP

Three human NPs (BNP, CNP, URO, and CU-NP were studied to evaluate their effects on vascular permeability as manifested by an increase in hematocrit. Normal anesthetized dogs received i.v. infusions of BNP (n=7), CNP (n=6), URO (n=5), or CU-NP (n=6) at 14 pmol/kg/minute. Blood was collected in EDTA tubes on ice and centrifuged. Data are reported for base-line and at 60 minutes of infusion. In addition to increasing hematocrit (Table 5), CU-NP reduced PCW pressure in vivo (baseline 6±0.9 mmHg, 60 minutes 3±0.9 mmHg; $P<0.05$). Thus, hemoconcentrating effects of CU-NP may contribute to its cardiac-unloading actions in vivo.

TABLE 5

CU-NP effects on hematocrit

| | Hematocrit (mean ± SEM; %) | |
|---|---|---|
| Treatment | Baseline | 60 min |
| BNP | 36 ± 1 | 40 ± 2* |
| CNP | 36 ± 1 | 37 ± 1 |
| URO | 37 ± 1 | 40 ± 1* |
| CU-NP | 38 ± 1 | 41 ± 1[†] |

(*= $P < 0.05$; [†]= $P < 0.01$)

Example 7

Cardiorenal and Neurohumoral Actions of CU-NP in Canine Experimental Heart Failure CU-NP was evaluated in canine heart failure (HF) to determine whether CU-NP would activate the second messenger cGMP and exert favorable actions without excessive hypotension. Mild HF was induced by pacing (180 bpm for 10 days). CU-NP was intravenously infused into 6 anesthetized dogs at 75 ng/kg/minute for 75 minutes. GFR was measured by inulin clearance. Fractional reabsorption of $Na^+$ (FRNa) was assessed by $Li^+$ clearance. Data were collected at pre-infusion (pre-I), 30 and 60 minutes I, and post-I. Plasma renin activity, angiotensin II, aldosterone, and cGMP also were measured. Results (mean±SEM) are presented in Table 6.

CU-NP increased plasma cGMP, urinary cGMP excretion, net renal cGMP generation, urine flow, and urinary $Na^+$ excretion. Proximal and distal FRNa were reduced. Renal blood flow and GFR were enhanced, with a mild decrease in MAP. Both CO and SVR were unchanged. PCWP and PAP were reduced. Plasma renin activity, angiotensin II, and aldosterone also were suppressed. Thus, CU-NP activated cGMP in canine HF and exerted renal-enhancing, cardiac-unloading and Renin-Angiotensin-Aldosterone System-suppressing actions without excessive hypotension.

TABLE 6

Renal and cardiovascular data for CU-NP in experimental HF

| | Pre-Infusion | 30 minutes | 60 minutes | Post-Infusion |
|---|---|---|---|---|
| GFR (mL/min) | 40 ± 5 | 51 ± 9 | 51 ± 3 | 53 ± 7* |
| Urine flow (mL/min) | 0.09 ± 0.01 | 0.50 ± 0.15[†] | 0.56 ± 0.11[†] | 0.19 ± 0.03 |
| $Na^+$ excretion (μEq/min) | 2.9 ± 0.9 | 80.5 ± 29.4[†] | 102.0 ± 22.2[†] | 22.1 ± 7.9 |
| $PFR_{Na+}$ (%) | 89 ± 2 | 68 ± 5[†] | 67 ± 3[†] | 79 ± 3* |
| $DFR_{Na+}$ (%) | 99.6 ± 0.1 | 96 ± 1[†] | 96 ± 1[†] | 99 ± 0.3 |
| Renal generation of cGMP (pmol/min) | 610 ± 66 | 2977 ± 549[†] | 3255 ± 662[†] | 1342 ± 200 |
| Plasma cGMP (pmol/mL) | 17 ± 3 | 41 ± 3[†] | 43 ± 2[†] | 21 ± 2 |
| Urinary cGMP excretion (pmol/min) | 1186 ± 152 | 5066 ± 826[†] | 5476 ± 876[†] | 2394 ± 197 |
| PCWP (mmHg) | 11 ± 1 | 9 ± 1[†] | 8 ± 1[†] | 10 ± 1 |
| PAP (mmHg) | 16 ± 0.8 | 15 ± 0.6* | 14 ± 0.7[†] | 16 ± 0.7 |
| Plasma renin activity (ng/mL/hour) | 9 ± 2 | 3 ± 1[†] | 2 ± 1[†] | 9 ± 2 |
| Angiotensin II (pg/mL) | 32 ± 7 | 9 ± 2[†] | 9 ± 3[†] | 19 ± 4 |
| Aldosterone (ng/dL) | 14 ± 5 | 9 ± 2 | 6 ± 2* | 11 ± 3 |
| RBF (mL/min) | 238 ± 39 | 281 ± 42* | 294 ± 42[†] | 275 ± 42* |

TABLE 6-continued

Renal and cardiovascular data for CU-NP in experimental HF

| | Pre-Infusion | 30 minutes | 60 minutes | Post-Infusion |
|---|---|---|---|---|
| MAP (mmHg) | 108 ± 9 | 100 ± 8† | 96 ± 8† | 107 ± 8 |
| CO (L/min) | 2.4 ± 0.1 | 2.5 ± 0.1 | 2.4 ± 0.1 | 2.3 ± 0.04 |
| SVR (mmHg · L$^{-1}$ · Min) | 42 ± 3 | 39 ± 3 | 39 ± 3 | 45 ± 3 |

*= P < 0.05 vs. pre-I;
†= P < 0.01 vs. pre-I;
GFR = glomerular filtration rate; PFR$_{Na+}$ = proximal fractional reabsorption of sodium; DFR$_{Na+}$ = distal fractional reabsorption of sodium; PCWP = pulmonary capillary wedge pressure; PAP = pulmonary arterial pressure; RBF = renal blood flow; MAP = mean arterial pressure; CO = cardiac output; SVR = systemic vascular resistance.

Example 8

In Vivo Effects of CU-NP on Renal Perfusion Pressure

Studies were conducted to determine the in vivo actions of CNP, CU-NP and URO on renal perfusion pressure (RPP, as estimated by MAP-RAP), as RPP is a key determinant of renal function. Given the GFR-enhancing action of CU-NP, in vitro studies also were done to test the hypothesis that CU-NP (unlike CNP) also activates NPR-A, a potent renal acting NP receptor.

Equimolar doses of CU-NP, human CNP, or human URO were intravenously infused at 14.14 pmol/kg/minute into 17 normal anesthetized dogs for 75 minutes. RPP was assessed at baseline and at 60 minutes of infusion. Data are expressed as mean±SEM. Clearances were measured from the 16th to the 45th minute and from the 46th to the 75th minute following initiation of peptide infusion. Within each group, 2-tailed paired t-test was used to compare RPP at 60 minutes of peptide infusion vs. baseline. Comparisons between groups were made by two-way ANOVA followed by Bonferroni post-test.

cGMP responses to the 3 peptides also were assessed in glomeruli isolated from canine kidneys upon harvest, in the presence or absence of an NPR-A antagonist, A719153 (1 μM), or an NPR-B antagonist, P194 (1 μM), or both antagonists added sequentially (A71915 followed by P194, 1 μM final concentration for both). To confirm the involvement of NPR-B in the cGMP response to CU-NP, additional experiments were conducted using human aortic endothelial cells (HAEC). Cyclic GMP response was determined by incubating CU-NP (10$^{-6}$ M) for 10 minutes in the absence or presence of an antibody to the ligand-binding domain of NPR-B. In vitro data (mean±SEM) were analyzed by one-way ANOVA followed by Bonferroni's post-test. Statistical significance was defined as P<0.05. GraphPad Prism 4 (GraphPad Software, San Diego, Calif.) was used for statistical analyses.

Figure 2:
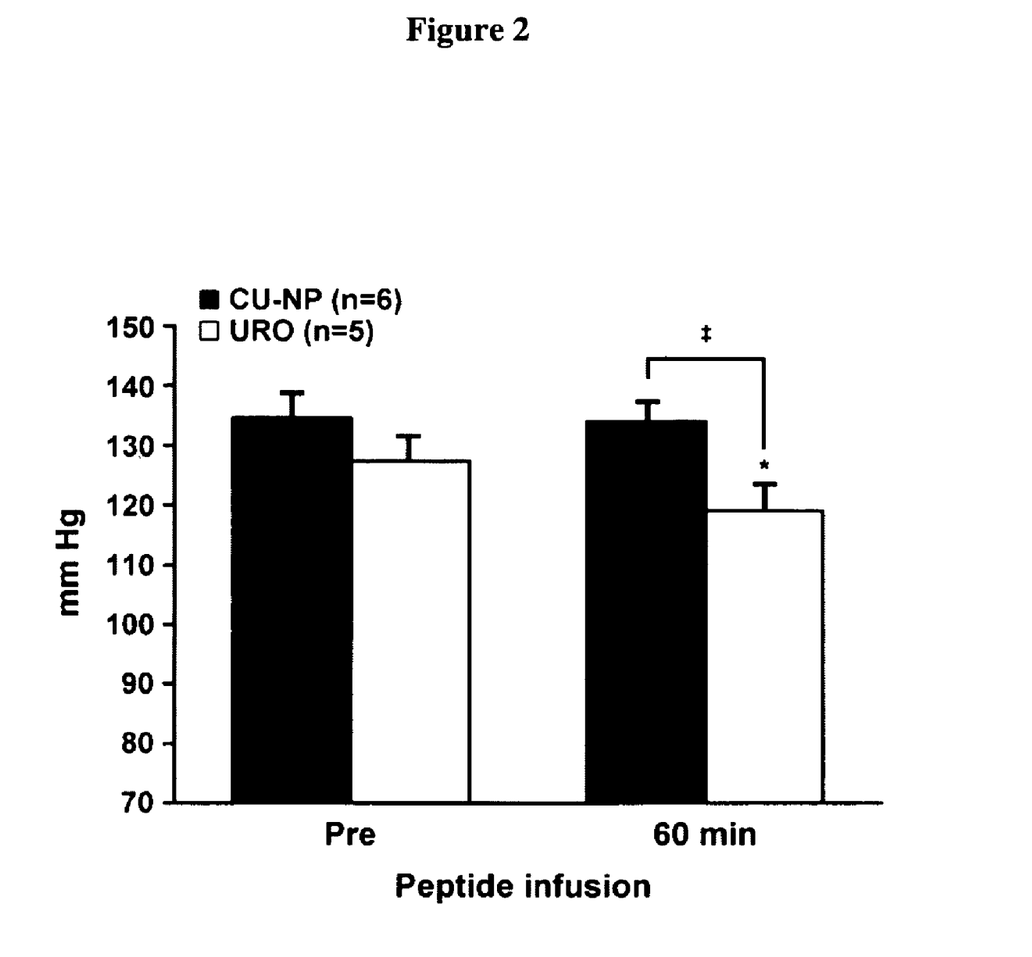
FIG. 2 is a graph plotting Renal Perfusion Pressure (as estimated by RPP=MAP−RAP) of normal anesthetized dogs treated with CU-NP or URO as indicated (mean±SEM; *=P<0.05 vs. baseline; ‡=P<0.05 between groups).

In the in vivo studies, RPP (mmHg) was preserved with CU-NP as compared to URO. When the two groups were compared, RPP was significantly lower with URO vs. CU-NP at 60 minutes of peptide infusion (P<0.05, FIG. 2). RPP was unchanged by CNP.

TABLE 7

CU-NP effects on RPP

| | RPP (mean ± SEM; mmHg) | |
|---|---|---|
| Treatment | Pre-I | 60 minutes |
| CNP | 120 ± 4 | 123 ± 8 |
| URO | 127 ± 4 | 119 ± 4* |
| CU-NP | 135 ± 4 | 134 ± 4 |

*= P = 0.05 vs. baseline

Figure 3:
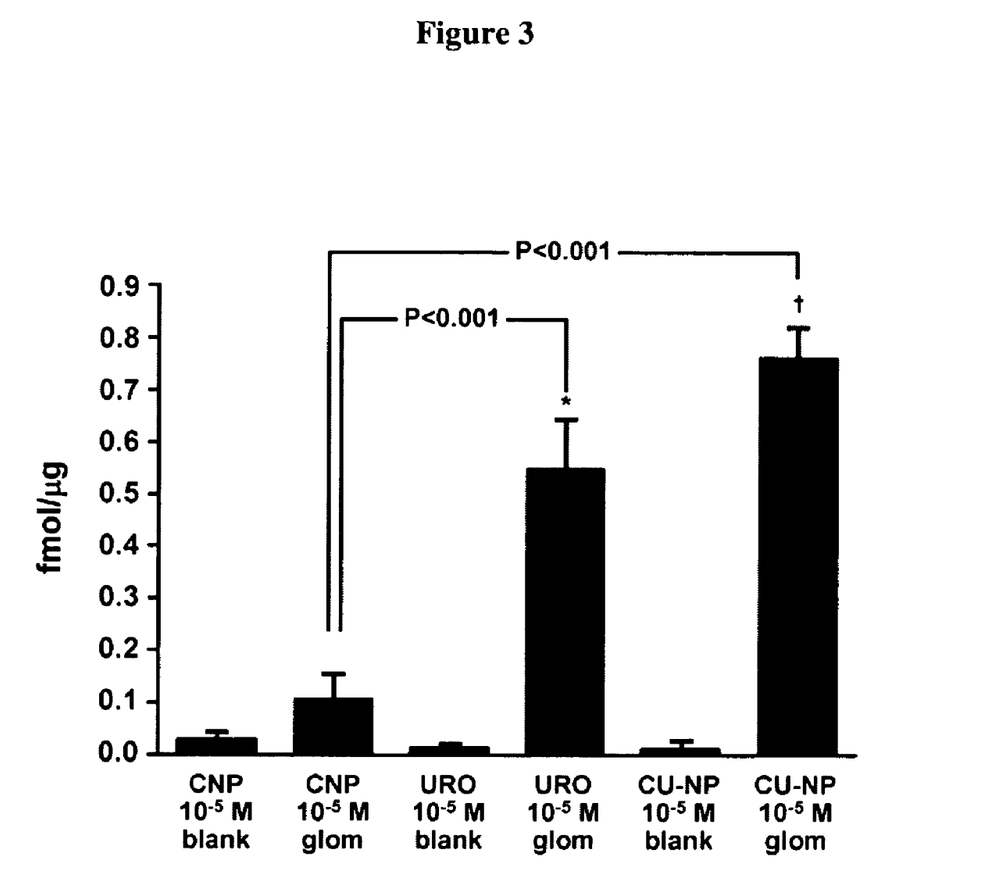
FIG. 3 is a graph plotting the cGMP response to equimolar concentrations of CU-NP, CNP, and URO in isolated canine glomeruli (n=3-7 for blanks, i.e., control; n=5-8 for glomeruli, †=P<0.0001 vs. blank; *=P<0.01 vs. blank).
Figure 4:
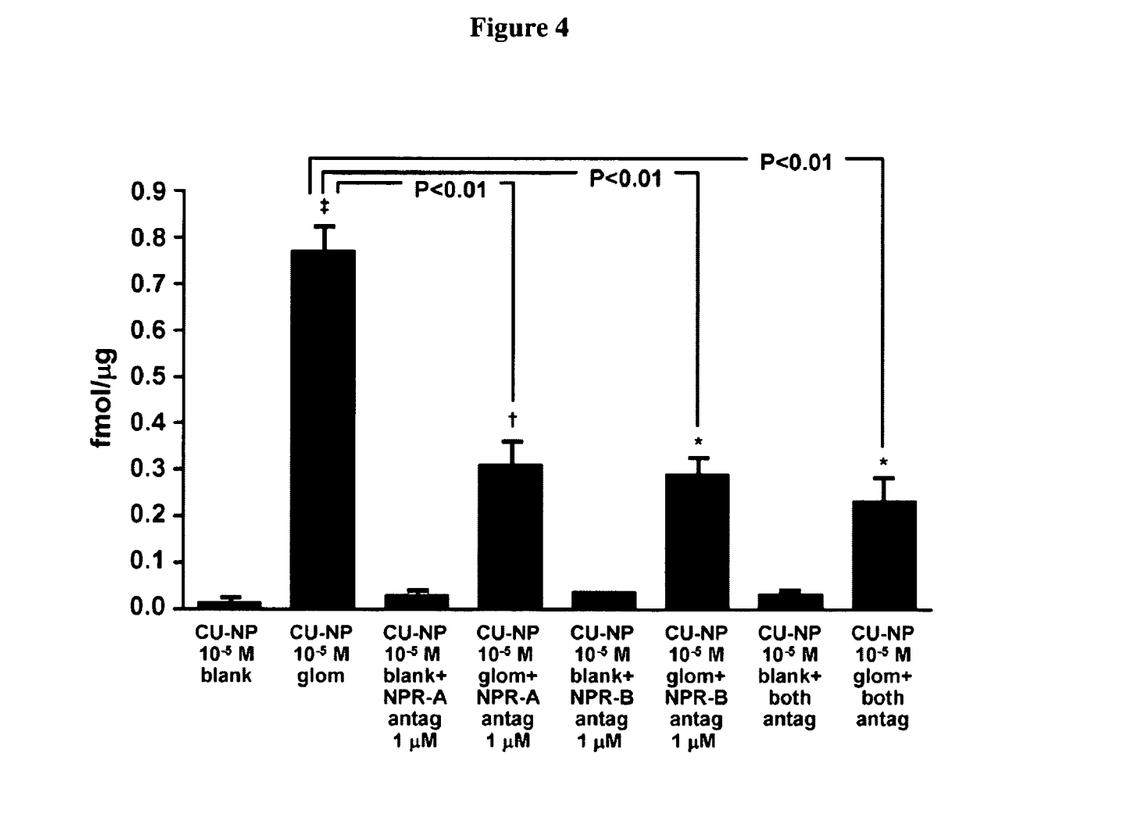
FIG. 4 is a graph plotting the cGMP response to equimolar concentrations of CU-NP in the presence or absence of an NPR-A antagonist (1 μM of A71915), an NPR-B antagonist (1 μM of P19), or both antagonists (A71915 followed by P19, final concentration 1 μM for both) as assessed in isolated canine glomeruli (n=2-4 for blanks; n=3-6 for glomeruli; *=P<0.05 vs. blank; †=P<0.01 vs. blank; ‡=P<0.0001 vs. blank).

In vitro, 10$^{-5}$ M CU-NP increased cGMP 7-fold vs. CNP (0.76±0.054‡ fmol/μg vs. 0.11±10.05 fmol/μg), with a trend to activate cGMP even more than URO (0.54±0.10 fmol/μg; P=0.086). These results are illustrated in FIG. 3. The cGMP-stimulating action of CU-NP was attenuated by blockade of NPR-A with A71915 (0.31±0.05† fmol/μg), blockade of NPR-B with P19 (0.28±0.04† fmol/μg), or blockade of both NPR-A and NPR-B with A71915 and P19 (0.23±0.05† fmol/μg), as shown in FIG. 4.

Figure 5:
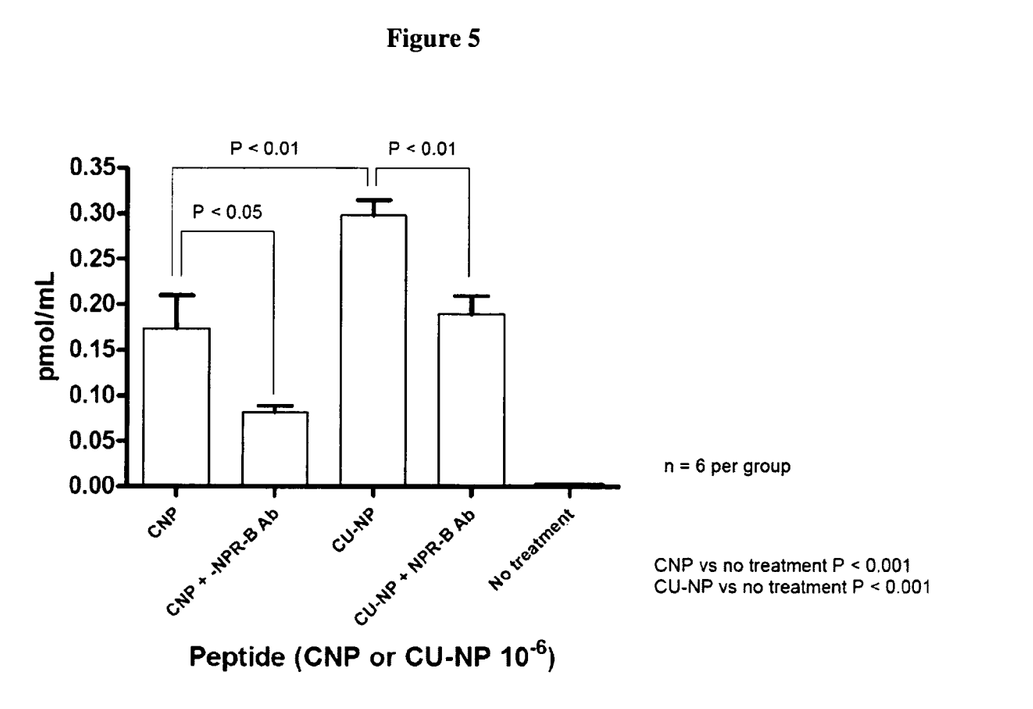
FIG. 5 is a graph plotting the cGMP response to CNP or CU-NP in the absence or presence of an NPR-B Antibody (1:100) as assessed in human aortic endothelial cells.

In HAEC, 10$^{-6}$ M CU-NP and CNP increased cGMP to 0.30±0.02 pmol/mL and 0.17±0.04 pmol/mL, respectively (P<0.01 for CU-NP vs. CNP; P<0.001 for CU-NP vs. control; P<0.001 for CNP vs. control). In the presence of the NPR-B antibody (1:100), the cGMP responses were attenuated to 0.19±0.02 pmol/mL for CU-NP and 0.08±0.01 pmol/mL for CNP (P<0.01 for CU-NP vs. no antibody and P<0.05 for CNP vs. no antibody). Results are plotted in FIG. 5. These data suggest that NPR-B is involved, at least in part, in the cGMP response to CU-NP.

Thus, CU-NP preserves RPP at renal enhancing doses, in contrast to URO, which reduces RPP. Further, in isolated glomeruli the actions of CU-NP involve co-activation of both NPR-A and NPR-B, representing a novel dual NP receptor activator in the kidney. NPR-B is involved in part in the cGMP response to CU-NP in human aortic endothelial cells. Thus, CU-NP represents a novel new peptide technology that is capable of dual NPR-A and NPR-B activation.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A polypeptide less than 36 amino acid residues in length, wherein said polypeptide comprises, in an order from amino terminus to carboxy terminus:
   (a) the sequence set forth in SEQ ID NO:1 or the sequence set forth in SEQ ID NO:1 with no more than one addition, subtraction, or substitution,
   (b) the sequence set forth in SEQ ID NO:2 or the sequence set forth in SEQ ID NO:2 with no more than two additions, subtractions, or substitutions, and
   (c) the sequence set forth in SEQ ID NO:3 or the sequence set forth in SEQ ID NO:3 with no more than one addition, subtraction, or substitution.

2. The polypeptide of claim 1, wherein said polypeptide comprises natriuretic activity.

3. The polypeptide of claim 1, wherein said polypeptide lacks the ability to induce systemic hypotension.

4. The polypeptide of claim 1, wherein said polypeptide comprises, in an order from amino terminus to carboxy terminus:
   (a) the sequence set forth in SEQ ID NO:1,
   (b) the sequence set forth in SEQ ID NO:2 or the sequence set forth in SEQ ID NO:2 with no more than two additions, subtractions, or substitutions, and
   (c) the sequence set forth in SEQ ID NO:3 or the sequence set forth in SEQ ID NO:3 with no more than one addition, subtraction, or substitution.

5. The polypeptide of claim 1, wherein said polypeptide comprises, in an order from amino terminus to carboxy terminus:
   (a) the sequence set forth in SEQ ID NO:1 or the sequence set forth in SEQ ID NO:1 with no more than one addition, subtraction, or substitution,
   (b) the sequence set forth in SEQ ID NO:2, and (c) the sequence set forth in SEQ ID NO:3 or the sequence set forth in SEQ ID NO:3 with no more than one addition, subtraction, or substitution.

6. The polypeptide of claim 1, wherein said polypeptide comprises, in an order from amino terminus to carboxy terminus:
   (a) the sequence set forth in SEQ ID NO:1 or the sequence set forth in SEQ ID NO:1 with no more than one addition, subtraction, or substitution,
   (b) the sequence set forth in SEQ ID NO:2 or the sequence set forth in SEQ ID NO:2 with no more than two additions, subtractions, or substitutions, and
   (c) the sequence set forth in SEQ ID NO:3.

7. A polypeptide comprising the sequence set forth in SEQ ID NO:4.

8. The polypeptide of claim 1, wherein said polypeptide comprises, in an order from amino terminus to carboxy terminus:
   (a) the sequence set forth in SEQ ID NO:1 with no more than one addition, subtraction, or substitution,
   (b) the sequence set forth in SEQ ID NO:2 or the sequence set forth in SEQ ID NO:2 with no more than two additions, subtractions, or substitutions, and
   (c) the sequence set forth in SEQ ID NO:3 or the sequence set forth in SEQ ID NO:3 with no more than one addition, subtraction, or substitution.

9. The polypeptide of claim 1, wherein said polypeptide comprises, in an order from amino terminus to carboxy terminus:
   (a) the sequence set forth in SEQ ID NO:1 or the sequence set forth in SEQ ID NO:1 with no more than one addition, subtraction, or substitution,
   (b) the sequence set forth in SEQ ID NO:2 with no more than two conservative amino acid substitutions, and
   (c) the sequence set forth in SEQ ID NO:3 or the sequence set forth in SEQ ID NO:3 with no more than one addition, subtraction, or substitution.

10. The polypeptide of claim 1, wherein said polypeptide comprises, in an order from amino terminus to carboxy terminus:
    (a) the sequence set forth in SEQ ID NO:1 or the sequence set forth in SEQ ID NO:1 with no more than one addition, subtraction, or substitution,
    (b) the sequence set forth in SEQ ID NO:2 or the sequence set forth in SEQ ID NO:2 with no more than two additions, subtractions, or substitutions, and
    (c) the sequence set forth in SEQ ID NO:3 with no more than one addition, subtraction, or substitution.

11. The polypeptide of claim 1, wherein said polypeptide is a substantially pure polypeptide.

12. The polypeptide of claim 7, wherein said polypeptide comprises natriuretic activity.

13. The polypeptide of claim 7, wherein said polypeptide lacks the ability to induce systemic hypotension.

14. The polypeptide of claim 7, wherein said polypeptide is a substantially pure polypeptide.

15. A pharmaceutical composition comprising a pharmaceutically acceptable carrier and the polypeptide of claim 7.

16. A pharmaceutical composition comprising a pharmaceutically acceptable carrier and the polypeptide of claim 1.

17. A method for increasing natriuretic activity within a mammal without lowering blood pressure, wherein said method comprises administering a polypeptide of claim 1 to said mammal.

18. A method for treating a mammal having a cardiovascular condition or renal condition, wherein said method comprises administering to said mammal a polypeptide of claim 1 under conditions wherein the severity of a manifestation of said cardiovascular condition or renal condition is reduced.

19. The method of claim 18, wherein administration of said polypeptide to said mammal does not lower the blood pressure of said mammal.

* * * * *